United States Patent
Carr et al.

(10) Patent No.: US 8,934,953 B2
(45) Date of Patent: Jan. 13, 2015

(54) DUAL MODE TEMPERATURE TRANSDUCER WITH OXYGEN SATURATION SENSOR

(75) Inventors: Kenneth L. Carr, Woolwich, ME (US); Robert C. Allison, Rancho Palos Verdes, CA (US)

(73) Assignee: Meridian Medical Systems, LLC, Portland, ME (US)

( * ) Notice: Subject to any disclaimer, the term of this patent is extended or adjusted under 35 U.S.C. 154(b) by 278 days.

(21) Appl. No.: 13/459,391

(22) Filed: Apr. 30, 2012

(65) Prior Publication Data
US 2012/0283534 A1    Nov. 8, 2012

Related U.S. Application Data

(60) Provisional application No. 61/482,269, filed on May 4, 2011.

(51) Int. Cl.
| | |
|---|---|
| A61B 5/00 | (2006.01) |
| A61B 5/0205 | (2006.01) |
| A61B 5/01 | (2006.01) |
| A61B 5/1455 | (2006.01) |
| A61F 7/00 | (2006.01) |

(52) U.S. Cl.
CPC .............. *A61B 5/02055* (2013.01); *A61B 5/01* (2013.01); *A61B 5/14553* (2013.01); *A61B 5/6814* (2013.01); *A61B 2562/0233* (2013.01); *A61F 2007/0002* (2013.01); *A61F 2007/0056* (2013.01); *A61F 2007/0095* (2013.01)
USPC .......................................... 600/329; 600/549

(58) Field of Classification Search
USPC .................................................. 600/323, 549
See application file for complete search history.

(56) References Cited

U.S. PATENT DOCUMENTS

| | | | |
|---|---|---|---|
| 5,683,381 A | 11/1997 | Carr et al. | |
| 8,062,228 B2 | 11/2011 | Carr | |
| 2006/0020185 A1* | 1/2006 | Al-Ali | 600/323 |
| 2012/0029359 A1* | 2/2012 | Sterzer et al. | 600/474 |

OTHER PUBLICATIONS

Product Package for Somanetics Corp. Model SPFTS Pediatric Somasensor, Mar. 11, 2011.

* cited by examiner

*Primary Examiner* — Max Hindenburg
*Assistant Examiner* — Renee Danega
(74) *Attorney, Agent, or Firm* — Cesari and McKenna, LLP

(57) ABSTRACT

Apparatus for detecting intracranial temperature and blood oxygenation includes a transducer having a working surface for placement against a patient's cranium. The transducer forms a microwave antenna having walls defining an aperture having a pair of opposite broader boundaries and a pair of opposite narrower boundaries at the working surface. The antenna is tuned to a frequency which produces a first output signal indicative of heat emanating from the cranium. An oxygen saturation sensor sharing that aperture includes a radiation emitter located at one of narrower boundaries which directs electromagnetic radiation across the aperture to a radiation detector at the other of the narrower boundaries and which produces a corresponding second output signal. A control unit includes a display and a processor for processing the signals to calculate an intracranial temperature and an oxygen saturation value for display by the control unit.

8 Claims, 5 Drawing Sheets

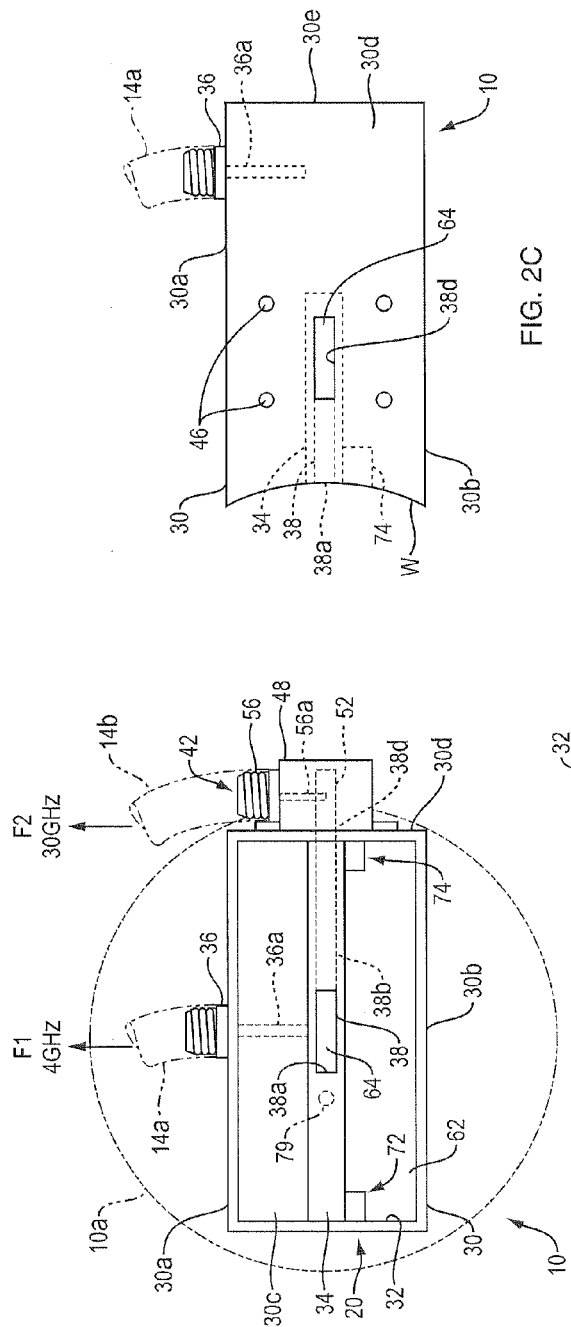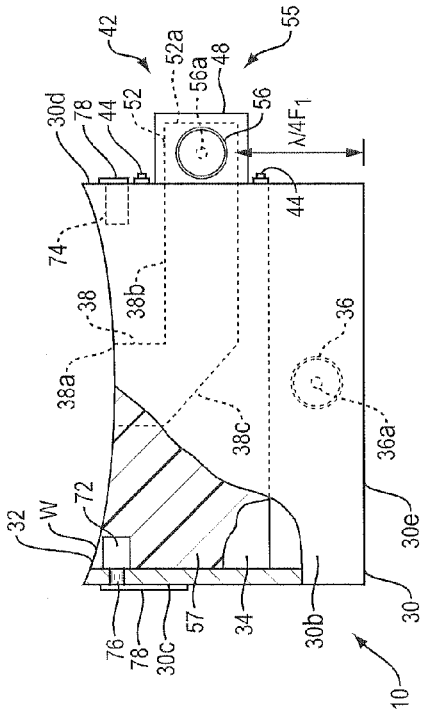

DUAL MODE TEMPERATURE TRANSDUCER WITH OXYGEN SATURATION SENSOR

RELATED APPLICATIONS

This application claims the benefit of U.S. Provisional Application Ser. No. 61/482,269, filed May 4, 2011, the contents of which are incorporated herein by reference.

BACKGROUND OF THE INVENTION

1. Field of the Invention

This invention relates to apparatus for reliably detecting and monitoring the temperature of brain tissue, particularly of a neonatal patient, while also monitoring the oxygenation of that patient's blood hemoglobin.

2. Background Information

During pediatric cardiac surgery, it is usually necessary to obtain circulatory arrest so that no blood is flowing in the patient's blood vessels. In order to minimize the likelihood of injury to the patient's organs, particularly the brain, the patient is covered with a cooling blanket which reduces the patient's core temperature by hypothermic cooling prior to the actual surgery. During surgery, the patient's heart is stopped and the intent is to maintain a brain temperature in the range of 15-18° C. Operating time is normally between 15 and 30 minutes. If the surgical procedure extends beyond that time, the infant's chances of survival decrease.

During the operation, since the patient's heart is stopped, there is no longer cold blood circulating through the blood vessels of the brain. To prevent the patient's head being warmed by the ambient air of the operating room, during circulatory arrest, brain cooling is usually augmented by a cooling cap placed on the patient's head while a cooling fluid is circulated through the cap to maintain the desired brain temperature. Thus the hypothermic cooling in combination with temperature monitoring not only controls brain temperature but also controls the rate of cooling of the brain, as well as the rate to re-warm it.

In addition, during cardiac surgery, the oxygenation of the patient's hemoglobin is often monitored by an oximeter because the patient will not thrive with inadequate oxygenation. For this, a cerebral oxygen saturation sensor, in the form an adhesive strip, may be placed across the patient's forehead. A sensor such as this is available from Somanetics Corporation of Troy, Mich. The sensor includes a light source, usually a light-emitting diode (LED), which produces infrared wavelengths. Light from the sensor is passed across the patient's forehead from one side of the strip to a receiver, e.g., a photodiode, on the other side of the strip. The light that is not absorbed by the blood-perfused regional tissue under the sensor is picked up by the receiver. The absorbance of the infrared light differs significantly between the oxygen-bound (bright red) and oxygen-unbound (dark red) blood hemoglobin in the regional tissue. Therefore, the oxy/deoxy hemoglobin ratio, i.e., the regional oxygen saturation value (r $SO_2$), can be calculated and displayed. If the value is too low, steps may be taken to remedy that situation, e.g., by postponing the surgery or speeding up the surgery to restore blood circulation.

There has recently been developed an intracranial temperature detection apparatus designed especially for neonatal patients. It uses microwave radiometry to monitor intracranial temperature at depth and usually also near surface (skin) temperature thus enabling close control over the hypothermia process; see U.S. Pat. No. 8,062,228, the entire contents of which is hereby incorporated herein by reference. That apparatus employs a microwave transducer designed to be positioned on the neonate's forehead. However, if the patient is wearing a cooling cap as described above, there is no room to apply to the infant's forehead both the transducer and the aforesaid oxygen saturation sensor.

Accordingly, there is a need to provide apparatus that can monitor intracranial temperature at depth and desirably also near surface temperature, as well as oxygenation of blood hemoglobin all at the same time using a single transducer able to be affixed to a neonate's forehead even though that patient may be wearing a cooling cap.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

The invention description below refers to the accompanying drawings, in which:

FIG. 2A is a bottom plan view of the transducer in the FIG. 1 apparatus;

FIG. 2B is a front elevational view with parts broken away thereof;

FIG. 2C is a side elevational view thereof;

DETAILED DESCRIPTION OF ILLUSTRATIVE EMBODIMENTS

Figure 1:
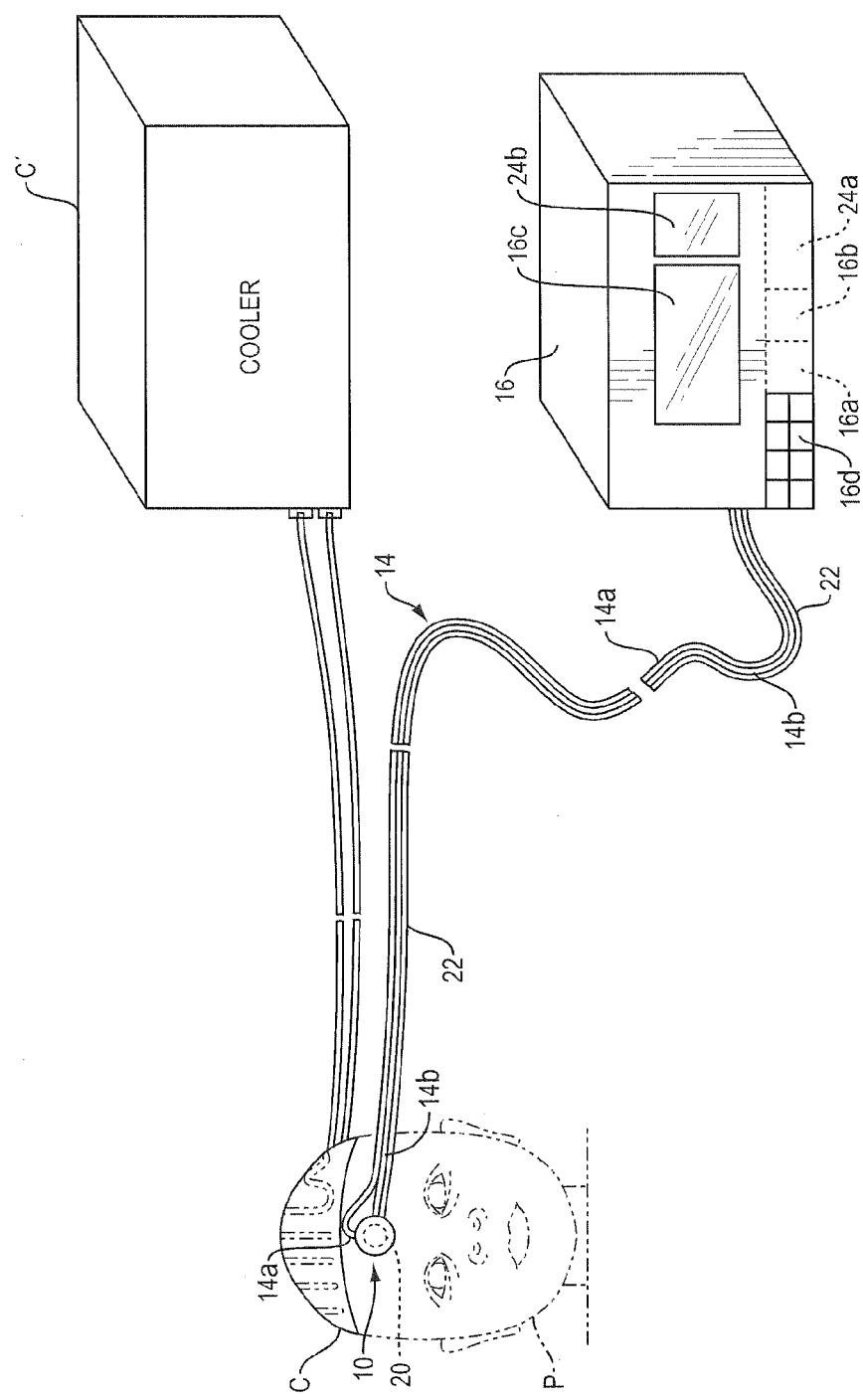
FIG. 1 is a diagrammatical view of monitoring apparatus comprising a dual mode temperature transducer with oxygen saturation sensing capability incorporating the invention.

Referring to FIG. 1 of the drawings, the present apparatus includes a transducer shown generally at 10 which may be removeably affixed to the forehead of a patient P, such as a neonate, in preparation for pediatric cardiac surgery. During such surgery, the patient preferably wears a cooling cap C connected via tubing to a cooler C' which circulates a cooling fluid through the cap to cool the patient's brain to maintain a low temperature in the order of 15-18° C.

As we shall see, transducer 10 contains a pair of microwave antennas capable of detecting thermal radiation originating from two different depths in the patient's cranium and producing corresponding output signals which are coupled via a cable 14 to a control unit 16. That unit includes a radiometric receiver 16a which, under the control of a programmable controller 16b, produces output signals which reflect the two intracranial temperatures in the patient P, namely the temperature at depth and the near surface temperature. Unit 16 may also include a display 16c which responds to those signals to provide a visible indication of the two temperatures. Unit 16 may be turned on and off and controlled by way of a keypad 16d.

The FIG. 1 apparatus also includes an oximeter or oxygen saturation sensor 20 in transducer 10 which is connected by a cable 22 to a processor 24a, which may be part of controller 16b, in unit 16. Processor 24a responds to signals from sensor 20 to compute the oxygenation percentage of the blood in the regional tissue under transducer 10 and deliver a corresponding control signal to a display 24b in unit 16 which thereupon displays that value.

Referring now to FIGS. 2A-2C, transducer 10 may comprise a first antenna in the form of a generally rectangular, electrically conductive waveguide 30 composed of a pair of mirror image-broader walls 30a and 30b, a pair of mirror-image narrow walls 30c and 30d and a rear wall 30e. Spaced from the end wall 30e is a front port or aperture 32 which is bounded by the edges of walls 30a-30d. The aperture and its boundary constitutes the working surface W of the transducer 10 and it may be slightly concave as shown in FIGS. 2B and 2C so that it more or less follows the curvature of the patient's forehead.

Waveguide 30 includes an electrically conductive septum 34 which extends between walls 30c and 30d so as to partition aperture 32 with little if any impact on the antenna pattern of the waveguide. Preferably, the septum extends from the working surface W toward end wall 30e a distance that allows for a coaxial connector 36 to be mounted to wall 30a so that its probe 36a can extend into waveguide 30 a sufficient distance to provide a waveguide-to-conductor transition that can couple electromagnetic energy from the waveguide 30 to produce a first output signal at connector 36 that corresponds to the thermal radiation picked up by waveguide antenna 30.

A second antenna in the form of a second, much smaller waveguide 38 may be present in septum 34. As best seen in FIG. 2B, the two waveguides 30 and 38 are coaxial and waveguide 38 has an aperture 38a that shares aperture 32 at working surface W. Waveguide 38 extends into septum 34 toward wall 30e and connects to a lateral waveguide segment 38b via a compact H plane right angle bend 38c. Segment 38b extends along septum 34 to a port 38d formed in the waveguide wall 30d.

As depicted in FIGS. 2A and 2B, the transducer 10 also includes a transition unit 42 which may be mounted to the waveguide wall 30d by threaded fasteners 44 turned down into threaded holes 46 in that wall. Unit 42 has been removed in FIG. 2C so that the holes 46 are visible there. The transition unit 42 comprises a housing 48 in which there is formed a waveguide extension 52 having an entrance aligned with port 38d in the waveguide wall 30d. The waveguide extension 52 includes an end wall 52a spaced opposite port 38d and which constitutes an end wall for the waveguide 38 as a whole. A coaxial connector 56 is mounted to the side of housing 48 so that its center conductor or probe 56a projects into waveguide extension 52 adjacent to its end wall 52a. Thus, electromagnetic energy may be coupled from waveguide 38 via the transition unit 42 to provide a signal corresponding to the near surface thermal radiation picked up by waveguide antenna 38.

Waveguides 30 and 38 are tuned to two different frequencies. More particularly, waveguide 30 operates at a relatively low frequency $F_1$, e.g. 4 GHz. Consequently, it has a relatively large antenna pattern which extends an appreciable distance from the waveguide aperture 32 and working surface W, i.e. at least 15 mm. On the other hand, waveguide 38 may be tuned to a much higher frequency $F_2$, e.g. 30 GHz and above, so that its antenna pattern, which is within the larger pattern, extends a much shorter distance from surface W, e.g. about 2 mm. In order to minimize the size of a transducer 10 operating at these frequencies, the waveguide 30 is preferably filled with a dielectric material 57 such as Delrin® acetal resin having a dielectric constant of 3.8. Likewise, the waveguide 38 may be filled with Teflon® tetraflouroethylene resin 59 having a dielectric constant of 2.1. Typically, waveguide 30 has an aperture 32 of 3.84×1.59 cm, while the waveguide 38 aperture 38a is 0.13×0.38 cm.

In order to separate the two different frequency signals from the microwave antennas 30 and 38, the probe 56a is spaced from end wall 30e of waveguide 30 a distance equal to a quarter wavelength λ/4, or integral multiple thereof, at the frequency $F_1$. This forms a quarter wave diplexer 55 as shown in FIG. 2B that is integrated into transducer 10.

If desired, the waveguide 30 may be mounted within a circular base or flange as shown in phantom at 10a in FIG. 2A so that the transducer has the general shape of a large aspirin tablet that can be affixed easily to the forehead of patient P as shown in FIG. 1.

Figure 3:
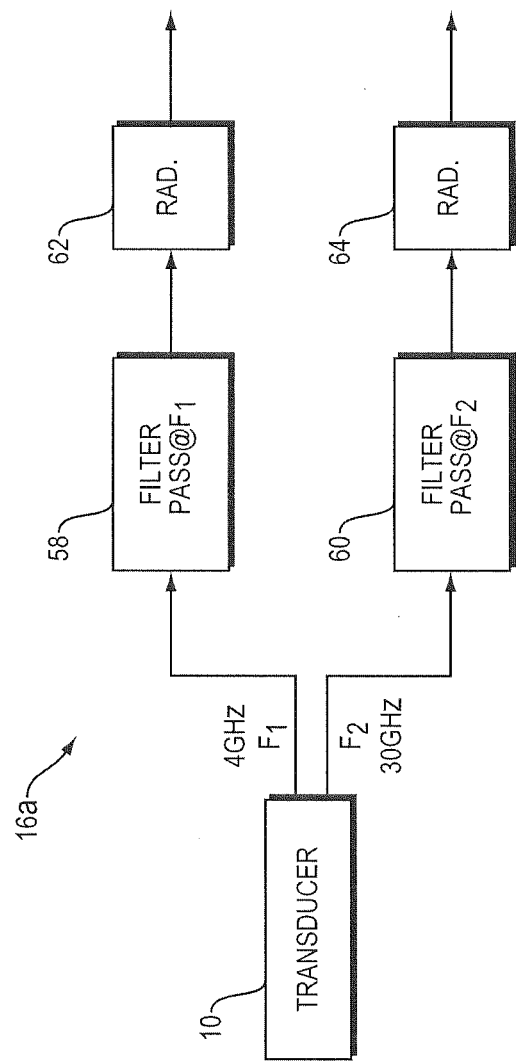
FIG. 3 is a block diagram of a radiometric receiver comprising the control unit of the FIG. 1 apparatus.

The cable 14 depicted in FIG. 1 actually comprises a pair of coaxial cables 14a and 14b releasably connected to connectors 36 and 56, respectively. As shown in FIG. 3, cables 14a and 14b couple the two output signals $F_1$ and $F_2$ from transducer 10 by way of filters 58 and 60, respectively, to a pair of radiometers 62 and 64 in receiver 16a of unit 16 to provide the temperature at depth and the near surface temperature indications that are displayed by the unit's display 16c as described in detail in the above-identified patent. The radiometers may be a known Dicke radiometer of the type described in U.S. Pat. No. 5,683,381.

It is a feature of this invention that in transducer 10, the oxygen saturation sensor 20 shares aperture 32 along with waveguide 38. As shown in FIGS. 2A-2C, sensor 20 comprises an infrared emitter unit 72 located adjacent to the working surface W at one side of waveguide 30 and an infrared detector unit 74 located adjacent the working surface at the opposite side of that waveguide. The spacing of units 72 and 74 is such that both units are located close to that waveguide's narrower walls or boundaries 30c and 30d where the E-field created in the waveguide 30 is at a minimum. Accordingly, they do not perturb the antenna pattern of the waveguide 30. In practice, the emitter and detector may be located at those boundaries anywhere from within septum 34 to adjacent one of the broader boundaries 30a and 30b. Electrical connections to and from sensor 20 may be taken out through insulated feedthroughs 76 in walls 30c and 30d as indicated in FIG. 2B, with any necessary sensor support circuitry 78 being located outside the waveguide aperture 32, in order to connect the emitter unit 72 and detector unit 74 to cable 22 leading to processor 24a in unit 16 (FIG. 1). The saturation sensor 20 may operate in a manner similar to the Somanetics sensor referred to above and will not be detailed here. Suffice it to say that the sensor's detector unit 74 produces an output signal that is applied to processor 24a enabling the processor to calculate the r $SO_2$ value of the regional tissue under transducer 10 and cause display 24b to display that value.

Also, instead of using a second waveguide antenna 38 in septum 34 along with the associated ancillary circuitry to measure the near surface temperature as described above, another type of temperature sensor shown in phantom at 79 in FIG. 2A, such as a thermistor, thermocouple or infrared detector, may be positioned in septum 34 at aperture 32 to provide the second output signal that signifies that temperature.

Also, the transducer depicted in FIGS. 2A-2C enables measurement of both intracranial and near surface temperatures. If only the former is required for particular applications, the septum 34 and the near surface temperature measurement sensor, e.g., waveguide 38, may be eliminated so that only infrared units 72 and 74 share aperture 32.

Figure 4A:
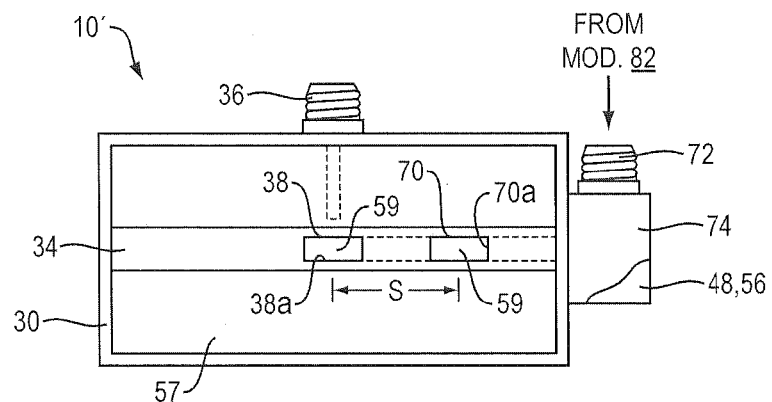
FIG. 4A is a view similar to FIG. 2A of another transducer embodiment.
Figure 4B:
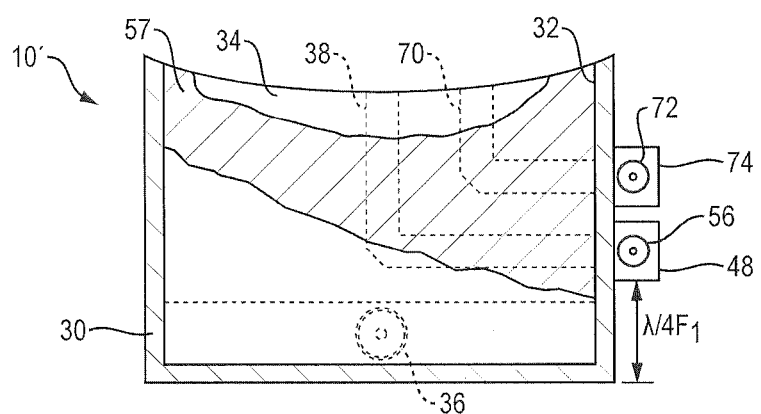
FIG. 4B is a view similar to FIG. 2B thereof.

Refer now to FIGS. 4A and 4B which disclose generally at 10' a transducer which is similar to transducer 10 except that it detects the amount of oxygen in blood using microwaves instead of electromagnetic radiation in the infrared region.

The transducer 10' has many elements in common with transducer 10. Therefore, these in-common elements carry the same identifying numerals.

Like transducer 10, transducer 10' includes a microwave antenna in the form of a dielectric-filled outer waveguide 30 with an electrically conductive septum 34 which partitions the waveguide 30 including its aperture 32. A waveguide connector 36 may couple electromagnetic energy from waveguide 30. As before, an output signal at this connector may be used to calculate the temperature at depth. A second antenna in the form of a waveguide 38 having an aperture 38a is present in septum 34. This waveguide leads to a coaxial connector 56 in a housing 48 on the outside of waveguide 30 to provide the output signal that is processed to calculate the near surface temperature. Thus, the transducer 10' operates in the same manner as the transducer 10 described above so that when placed on a patient P (FIG. 1), the transducer may detect the temperature at two different depths in the patient's cranium.

Transducer 10' can also detect the amount of oxygen present in the patient's regional tissue that underlies transducer 10 using microwaves instead of light in the infrared region. More particularly, transducer 10' includes a second waveguide 70 in septum 34 which extends from an aperture 70a at working surface W (FIG. 1) to a connector 72 in a housing 74 on the outside of waveguide 30 next to housing 48. The waveguide 70 may be similar to waveguide 38 and be filled with a dielectric material 59 so that the small dimension of waveguides 38 and 70 can be compatible with the width of the septum 34.

Figure 5:
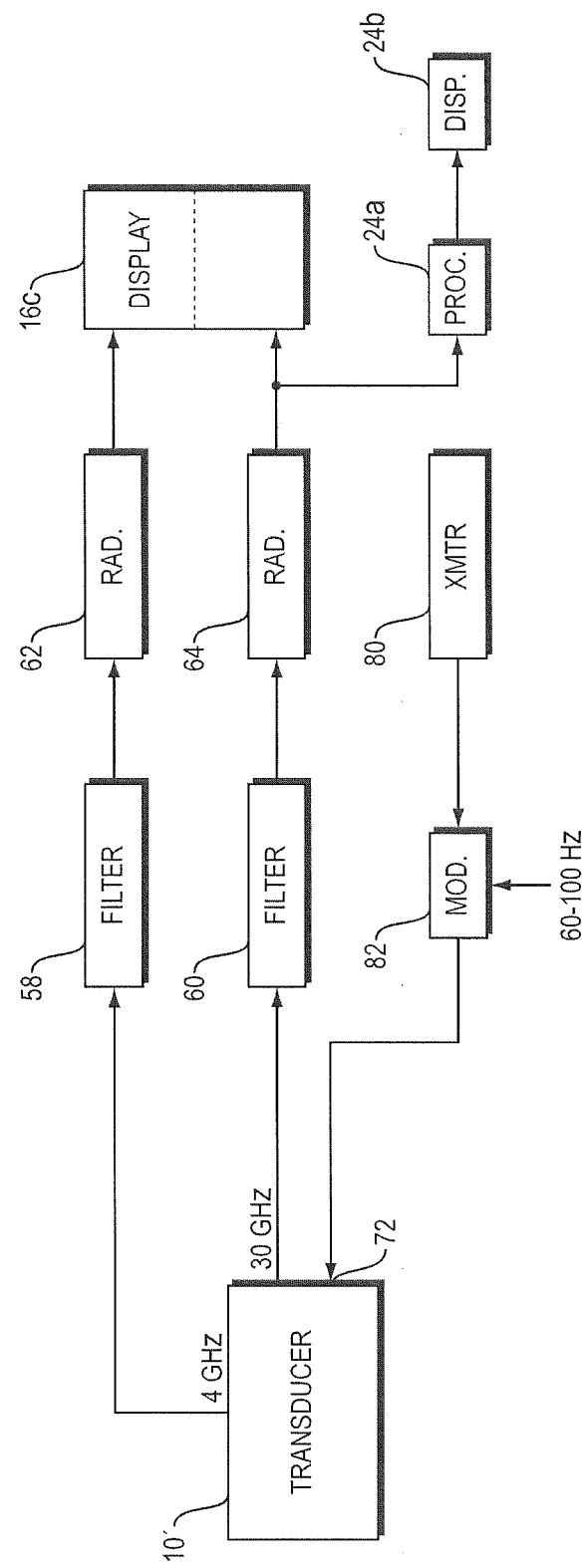
FIG. 5 is a view similar to FIG. 3 of a receiver for use with the FIGS. 4A and 4B transducer.

As shown in FIG. 5, connector 72 is connected to receive the output from a transmitter 80 in control unit 16 (FIG. 1) which transmits a signal at the same frequency as that to which the waveguides 38 and 70 are tuned, i.e., $F_2=30$ GHz and higher.

When the transducer 10' is positioned with its working surface against the patient's forehead as shown in FIG. 1, the signal from transmitter 80 that is applied to waveguide 70 will be coupled to the receiving waveguide 38 across the space S between the two antenna apertures 78a and 38a, respectively. That spacing S will depend on the frequency $F_2$ and the coupling required, the latter being dependent on the signal level of the transmitter 80 and the sensitivity of the radiometer 64 in receiver 16b.

The transducer 10' operates in a manner somewhat similar to that of transducer 10 in that the microwave signal coupled from the emitting waveguide 70 to the receiving waveguide 38 will depend upon the absorbance of the tissue underlying the transducer 10' and that, in turn, will depend upon the degree of oxygenation of the blood in that tissue. As the amount of oxygen in the blood hemoglobin changes, so will the absorbance of the tissue resulting in a change in the signal picked up by the receiving waveguide 38 and applied to the radiometer 64. The output of that radiometer is fed to processor 24a which calculates the r $SO_2$ value which value may be displayed by display 24b.

While transmitter 80 could be operated intermittently to provide an intermittent oxygenation measurement, to enable the system to measure the oxygen level at the same time that it is detecting the intracranial temperature(s) of the patient, the signal from transmitter 80 may be modulated by a modulator 82 at a low frequency, e.g., 60 to 110 Hz. In that event, the signal coupled to the receiving waveguide 38 and applied to radiometer 64 would be similarly modulated. That modulated signal may then be detected and processed in processor 24a to produce the oxygen saturation value described above. The same modulation procedure may be used for the oxygenation sensor 20 when an infrared detector is used to measure surface temperature as described above in order to facilitate simultaneous measurement of the $rSO_2$ value.

While the transducers 10 and 10' have antennas 30, 38 and 70 in the form of waveguides, those antennas may also be of a strip line structure as described in the above patent. In that event, the antennas in septum 34 may be tuned to a lower microwave frequency, e.g. 4 GHz, and the transmitter 80 would transmit at that frequency.

It will thus be seen that the objects set forth above, among those made apparent from the preceding description, are efficiently attained and, since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described.

What is claimed is:

1. An apparatus for detecting intracranial temperature and blood oxygenation in a patient, said apparatus comprising
    a transducer having a working surface for placement against a patient's cranium, said transducer including
    a microwave antenna defining an aperture at or near said working surface, said antenna being tuned to a first frequency that produces a first output signal indicative of heat emanating from within a cranium against which it is placed,
    an oxygen saturation sensor sharing said aperture, said sensor including an electromagnetic radiation emitter which directs electromagnetic radiation across the aperture to a radiation detector, said detector senses any radiation not absorbed by a cranium against which the transducer is placed and produces a corresponding second output signal, and
    a control unit connected to the transducer, said control unit including a display,
    a radiometer centered on said first frequency and which receives said first output signal and produces a corresponding temperature signal, and
    a processor to process the second output signal and calculate an oxygenation value for display by the control unit, and further
    wherein said antenna is a rectangular waveguide having a pair of opposite broader walls and a pair of opposite narrower walls which define broader and narrower boundaries of said aperture, and
    the emitter and detector are located opposite one another at said narrower boundaries.

2. The apparatus defined in claim 1 wherein the emitter and detector emit and detect infrared light, respectively.

3. The apparatus defined in claim 1,
    further including a septum extending between opposite locations on the narrower boundaries to partition said aperture, and
    wherein said emitter and said detector are located in the septum.

4. The apparatus defined in claim 1,
    further including a septum extending between opposite locations on the narrower boundaries to partition said aperture, and
    wherein said emitter and said detector are located between the septum and said broader boundaries.

5. The apparatus defined in claim 1 and further including a septum extending between opposite locations on the narrower boundaries to partition said aperture, and a heat sensor in the septum at or near said working surface for sensing the near surface temperature of a cranium against which the transducer is placed and producing a corresponding third output signal, said processor also processing said third output signal to calculate a near surface temperature value for display by the control unit.

6. The apparatus defined in claim 5 wherein the heat sensor is selected from the group consisting of thermocouple, thermister and infrared detector.

7. The apparatus defined in claim 5 wherein
the heat sensor includes a second microwave antenna having a second aperture shared with the aperture of said microwave antenna, said second antenna being tuned to a second frequency different from the first frequency, and
the control unit also includes a second radiometer centered on the second frequency and which receives said third output signal and produces a corresponding surface temperature signal which is processed by the processor to calculate a near surface temperature value for display by the control unit.

8. An apparatus for detecting intracranial temperature and blood oxygenation in a patient, said apparatus comprising
a transducer having a working surface for placement against a patient's cranium, said transducer including
a microwave antenna defining an aperture at or near said working surface, said antenna being tuned to a first frequency that produces a first output signal indicative of heat emanating from within a cranium against which it is placed,
an oxygen saturation sensor sharing said aperture, said sensor including an electromagnetic radiation emitter which directs electromagnetic radiation across the aperture to a radiation detector, said detector sense any radiation not absorbed by a cranium against which the transducer is placed and produces a corresponding second output signal, and
a control unit connected to the transducer, said control unit including a display,
a radiometer centered on said first frequency and which receives said first output signal and produces a corresponding temperature signal, and
a processor to process the second output signal and calculate an oxygenation value for display by the control unit, and further
wherein the apparatus includes a modulator which modulates the electromagnetic emissions from said emitter to facilitate detection of the second output signal by the radiometer.

* * * * *